US00PP11855P2

(12) United States Plant Patent
Glicenstein

(10) Patent No.: US PP11,855 P2
(45) Date of Patent: May 1, 2001

(54) CHRYSANTHEMUM PLANT NAMED 'YOMAGGIE'

(75) Inventor: Leon Glicenstein, State College, PA (US)

(73) Assignee: Yoder Brothers, Inc., Barberton, OH (US)

( * ) Notice: Subject to any disclaimer, the term of this patent is extended or adjusted under 35 U.S.C. 154(b) by 0 days.

(21) Appl. No.: 09/224,725

(22) Filed: Jan. 4, 1999

(51) Int. Cl.[7] ..... A01H 5/00

(52) U.S. Cl. ..... Plt./286

(58) Field of Search ..... Plt./286

*Primary Examiner*—Howard J. Locker
(74) *Attorney, Agent, or Firm*—C. A. Whealy

(57) ABSTRACT

A distinct cultivar of Chrysanthemum plant named 'Yomaggie', characterized by its uniformly mounded, broad and dense plant habit; shiny dark green leaves; quilled daisy-type inflorescences that are about 5.7 cm in diameter; attractive upright lavender, purple-tipped ray florets and bright yellow disc florets; and numerous inflorescences per plant.

1 Drawing Sheet

BACKGROUND OF THE INVENTION

The present invention relates to a new and distinct cultivar of Chrysanthemum plant, botanically known as *Dendranthema grandiflora* and referred to by the cultivar name Yomaggie.

The new cultivar is a product of a planned breeding program conducted by the Inventor in Salinas, Calif. The objective of the breeding program is to create new garden-type Chrysanthemum cultivars having inflorescences with desirable inflorescence forms and floret colors and good garden performance.

The new cultivar originated from a cross made by the Inventor in November, 1992, of two unidentified proprietary seedling selections.

The cultivar Yomaggie was discovered and selected by the Inventor as a flowering plant within the progeny of the stated cross in a controlled environment in Salinas, Calif., in August, 1993. The selection of this plant was based on its desirable inflorescence form and ray floret color.

Asexual reproduction of the new cultivar by terminal cuttings taken in a controlled environment in Salinas, Calif., has shown that the unique features of this new Chrysanthemum are stable and reproduced true to type in successive generations.

SUMMARY OF THE INVENTION

The cultivar Yomaggie has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Yomaggie'. These characteristics in combination distinguish 'Yomaggie' as a new and distinct cultivar:

1. Uniformly mounded, broad and dense plant habit.
2. Dark green shiny leaves.
3. Quilled daisy-type inflorescences that are about 5.7 cm in diameter.

4. Attractive upright lavender ray florets with purple apices and bright yellow disc florets.
5. Numerous inflorescences per plant.

The new Chrysanthemum is similar to the *Dendranthema grandiflora* cultivar Illusion, disclosed in U.S. Plant Pat. No. 6,644. However in side-by-side comparisons under commercial practice, plants of the new Chrysanthemum differed from plants of the cultivar Illusion in the following characteristics:

1. Plants of the new Chrysanthemum are shorter and more spreading than plants of the cultivar Illusion.
2. Plants of the new Chrysanthemum flower about two weeks later than plants of the cultivar Illusion under natural season conditions.
3. Ray florets of plants of the new Chrysanthemum are lavender with purple apices whereas ray florets of plants of the cultivar Illusion are white.

BRIEF DESCRIPTION OF THE PHOTOGRAPHS

The accompanying photographs illustrate the overall appearance of the new cultivar.

The photograph at the top of the sheet comprises a side perspective view of a typical flowering plant of 'Yomaggie'.

The photograph at the bottom of the sheet comprises a close-up view of typical inflorescences of the cultivar 'Yomaggie'. These photographs show the colors as true as it is reasonably possible to obtain in colored reproductions of this type. Floret and foliage colors in the photographs may differ from the actual colors due to light reflectance.

DETAILED BOTANICAL DESCRIPTION

In the following description, color references are made to The Royal Horticultural Society Colour Chart except where general terms of ordinary dictionary significance are used. The following observations and measurements describe plants grown in Leamington, Ontario, Canada, under conditions which approximate those generally used in commercial garden Chrysanthemum production. One rooted cutting was planted in a 15-cm container on Jul. 20, 1998 and plants were grown outdoors under natural season conditions. Measurements and numerical values represent averages for typical flowering containers.

Botanical classification: *Dendranthema grandiflora* cultivar Yomaggie.

Commercial classification: Daisy-type garden chrysanthemum.

Parentage:

*Female or seed parent.*—Unidentified proprietary seedling selection.

*Male or pollen parent.*—Unidentified proprietary seedling selection.

Propagation:

*Type.*—Terminal tip cuttings.

*Time to rooting.*—Seven to ten days with soil termperatures of 21° C.

*Rooting habit.*—Fine, fibrous and well-branched.

Plant description:

*Appearance.*—Perennial herbaceous daisy-type garden Chrysanthemum. Inverted triangle. Stems initially upright, then outwardly spreading giving a uniformly mounded appearance to the plant. Freely branching with lateral branches potentially developing at every node, when pinched, about 12 laterals develop.

*Plant height.*—About 29 cm.

*Plant spread.*—About 49 cm.

*Foliage description.*—Leaf arrangement: Alternate. Length: About 5.5 cm. Width: About 4.7 cm. Apex: Mucronate or rounded. Base: Attenuate to truncate. Margin: Palmately lobed, sinuses divergent. Texture: Upper surface sparsely pubescent; lower surface moderately pubescent. Veins prominent on lower surface. Petiole length: About 2.3 cm. Petiole diameter: About 3 mm. Color: Young foliage upper surface: 147A, shiny. Young foliage lower surface: Close to 147B. Mature foliage upper surface: 147A, shiny. Mature foliage lower surface: 147B. Venation upper surface: 147B. Venation lower surface: 147C.

Inflorescence description:

*Appearance.*—Daisy-type inflorescence form with flattened quill-shaped ray florets. Inflorescences borne on terminals above foliage, arising from leaf axils. Disk and ray florets arranged acropetally on a capitulum. One inflorescence per terminal with numerous inflorescences per plant, about 10 to 12 per lateral stem.

*Flowering response.*—Under natural season conditions, plants flower in early to mid October in the Northern Hemisphere about 89 days after planting, and flower for at least three weeks depending on weather conditions.

*Inflorescence bud before showing color.*—Height: About 6 mm. Diameter: About 7.5 mm. Phyllary color: Close to 141A.

*Inflorescence size.*—Diameter: About 5.7 cm. Depth (height): About 1.8 cm. Diameter of disc: About 1.5 cm.

*Ray florets.*—Shape: Flattened quill, straight, very long corolla tube. Length: About 2.7 cm. Width: About 2.5 mm. Apex: Dentate. Margin: No margin, fused tube. Texture: Smooth, glabrous. Orientation: Upright, positioned about 130° to the peduncle. Number of ray florets per inflorescence: About 63 in several rows. Color: When opening: Lavender, 69A to 69B; apices, close to 70A to 70B; throat, close to 70A to 70B. Opened inflorescence: Lavender, 69A to 69B; apices, close to 70A to 70B; throat, close to 70A to 70B.

*Disc florets.*—Shape: Tubular, apex dentate. Length: About 6 mm. Width: Apex: About 2 mm. Base: About 1 mm. Number of disc florets per inflorescence: Typically more than 150. Color: Immature: 154A to 5A. Mature: Apex: 9A to 14A. Mid-section: Greenish white. Base: White.

*Peduncle.*—Aspect: Flexible, angled about 45° to the stem. Length: First peduncle: About 5.1 cm. Fourth peduncle: About 5.9 cm. Diameter: About 3 mm. Texture: Pubescent. Color: Close to 144A.

*Reproductive organs.*—Androecium: Present on disc florets only. Anther color: 13A. Pollen: Scarce to moderate, 17A. Gynoecium: Present on both ray and disc florets.

Disease resistance: Resistance to known Chrysanthemum diseases has not been observed on plants grown under commercial production conditions.

Seed production: Seed production has not been observed.

It is claimed:

1. A new and distinct cultivar of Chrysanthemum plant named 'Yomaggie', as illustrated and described.

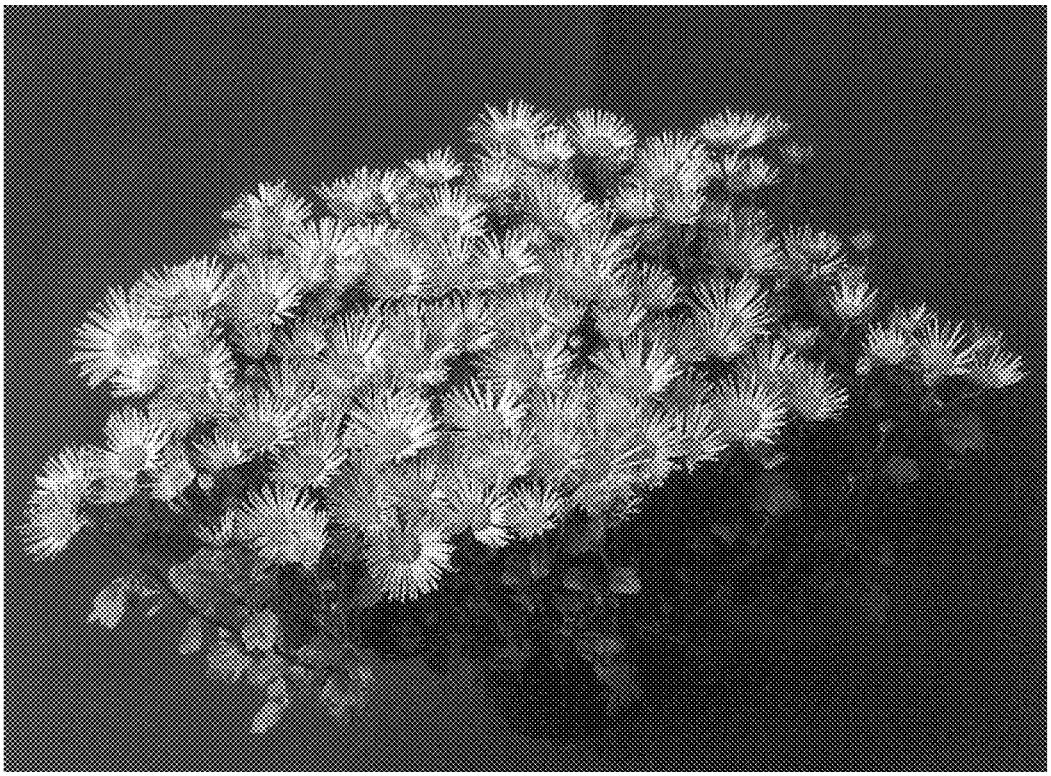
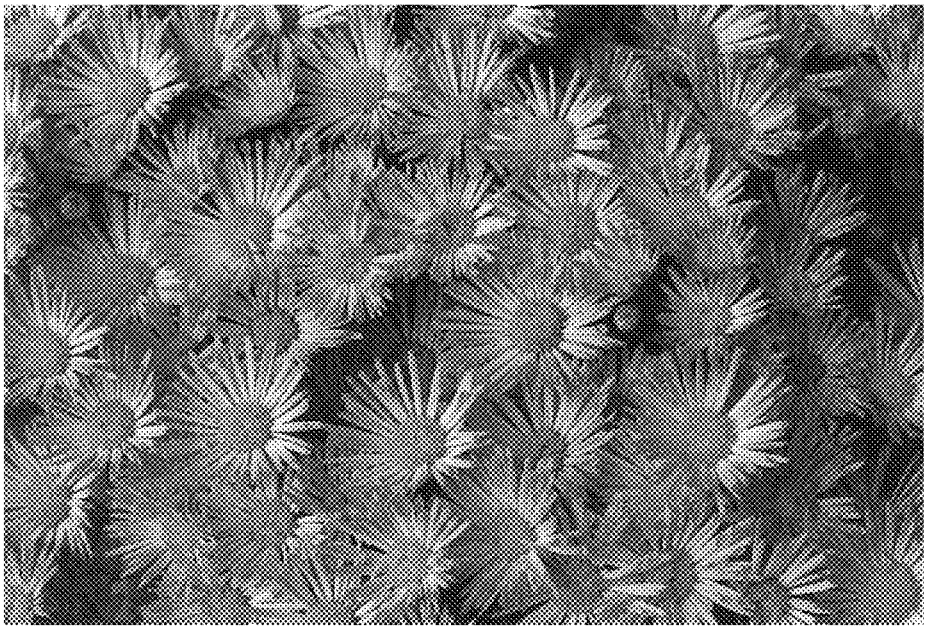

* * * * *